US00PP37023P2

(12) United States Plant Patent
Hofmann

(10) Patent No.: US PP37,023 P2
(45) Date of Patent: Oct. 14, 2025

(54) ***PETUNIA* PLANT NAMED 'INPETTIABL'**

(50) Latin Name: ***Petunia* X *hybrida***
Varietal Denomination: INPETTIABL

(71) Applicant: Birgit Hofmann, Rudesheim am Rhein (DE)

(72) Inventor: Birgit Hofmann, Rudesheim am Rhein (DE)

(73) Assignee: INNOVA PLANT ZIERPFLANZEN GmbH +Co. KG, Gensingen (DE)

( * ) Notice: Subject to any disclaimer, the term of this patent is extended or adjusted under 35 U.S.C. 154(b) by 0 days.

(21) Appl. No.: 18/755,408

(22) Filed: Jun. 26, 2024

(51) Int. Cl.
*A01H 6/82* (2018.01)

(52) U.S. Cl.
USPC ..... Plt./356.13

(58) Field of Classification Search
USPC ..... Plt./356.13
CPC . A01H 5/02; A01H 5/00; A01H 6/824; A01H 6/82
See application file for complete search history.

(56) References Cited

U.S. PATENT DOCUMENTS

PP31,331 P3 * 1/2020 Kleinwee ..... A01H 6/824 Plt./356.13

OTHER PUBLICATIONS

Garden Center Marketing Supertunia Tiara Blue, retrieved on Apr. 24, 2025 at https://www.gardencentermarketing.com/plantName/Petunia-hybrid-Supertunia-Tiara-blue?srsltid=AfmBOoqhOA2k2VyVHwaaLUGJWjXOyHSIkymEfAuNqy5b9R_XrRrd06AO, 4 pp. (Year: 2025).*

Hullett, Greenhouse Grower Stunning New Varieties at Proven Winners Open House 2024, retrieved on Apr. 21, 2025 at https://www.greenhousegrower.com/crops/stunning-new-varieties-at-proven-winners-open-house/, 4 pp. (Year: 2024).*

Syngenta Flowers Cuttings Collection 2019/2020, retrieved on Apr. 21, 2025 at http://www.gradinaspa.com/part/19%20Katalog%20SYNGENTA%20FLOWERS%20Cuttings%202019-2020.pdf, cover page, pp. 53-54, 104. (Year: 2019).*

* cited by examiner

*Primary Examiner* — June Hwu
(74) *Attorney, Agent, or Firm* — C. Anne Whealy

(57) ABSTRACT

A new and distinct *Petunia* plant named 'INPETTIABL', characterized by its upright to outwardly spreading and mounding plant habit to eventually trailing and decumbent plant habit; vigorous growth habit and rapid growth rate; freely branching habit; dense and bushy plant form; early and freely flowering habit; medium-sized single-type flowers that are dark violet in color with light purple-colored centers; and excellent container and garden performance.

2 Drawing Sheets

Figure 1:
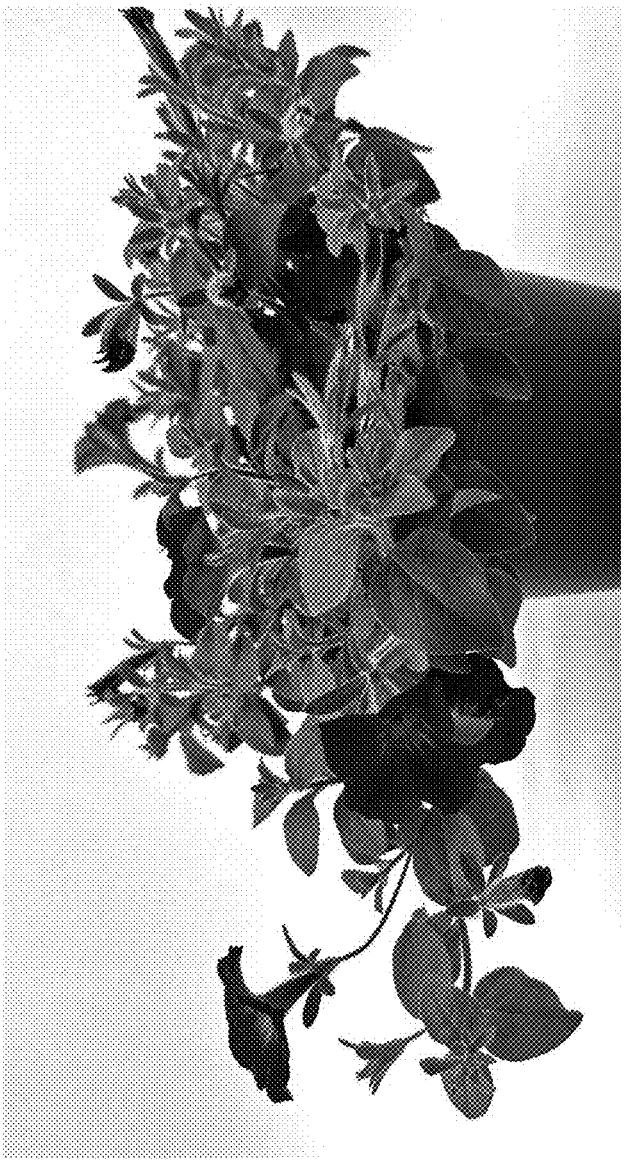

Botanical designation: *Petunia* X *hybrida.*
Cultivar denomination: 'INPETTIABL'.

BACKGROUND OF THE INVENTION

The present invention relates to a new and distinct cultivar of *Petunia* plant, botanically known as *Petunia* X *hybrida* and hereinafter referred to by the name 'INPETTIABL'.

The new *Petunia* plant is a product of a planned breeding program conducted by the Inventor in Heidesheim, Germany. The objective of the breeding program is to create new vigorous, freely-branching and uniformly mounding *Petunia* plants with early and freely flowering habit, attractive flowers and good garden performance.

The new *Petunia* plant originated from a cross-pollination made by the Inventor in June 2019 in Heidesheim, Germany of a proprietary selection of *Petunia* X *hybrida* identified as code number Pt18-4301-3, not patented, as the female, or seed, parent with a proprietary selection of *Petunia* X *hybrida* identified as code number Pt18-4313-8, not patented, as the male, or pollen, parent. The new *Petunia* plant was discovered and selected by the Inventor as a single flowering plant within the progeny of the stated cross-pollination in a controlled greenhouse environment in Heidesheim, Germany in May 2020.

Asexual reproduction of the new *Petunia* plant by vegetative terminal cuttings in a controlled greenhouse environment in Heidesheim, Germany since June 2020 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'INPETTIABL'. These characteristics in combination distinguish 'INPETTIABL' as a new and distinct *Petunia* plant:

1. Upright to outwardly spreading and mounding plant habit to eventually trailing and decumbent plant habit.
2. Vigorous growth habit and rapid growth rate.
3. Freely branching habit; dense and bushy plant form.

4. Early and freely flowering habit.
5. Medium-sized single-type flowers that are dark violet in color with light purple-colored centers.
6. Excellent container and garden performance.

Plants of the new *Petunia* can be compared to plants of the female parent selection. In side-by-side comparisons, plants of the new *Petunia* differ primarily from plants of the female parent selection in the following characteristics:

1. Plants of the new *Petunia* are more freely branching and denser than and not as open as plants of the female parent selection.
2. Plants of the new *Petunia* have darker green-colored leaves than plants of the female parent selection.
3. Plants of the new *Petunia* have larger flowers than plants of the female parent selection.
4. Flowers of plants of the new *Petunia* are dark violet in color with light purple-colored centers whereas flowers of plants of the female parent selection are purplish lilac in color.
5. Flowers of plants of the new *Petunia* are bright in color and resist fading whereas flowers of plants of the female parent selection are dull in color and readily fade with subsequent development.

Plants of the new *Petunia* can be compared to plants of the male parent selection. In side-by-side comparisons, plants of the new *Petunia* differ primarily from plants of the male parent selection in the following characteristics:

1. Plants of the new *Petunia* are more trailing than and not as upright as plants of the male parent selection.
2. Plants of the new *Petunia* have darker green-colored leaves than plants of the male parent selection.
3. Plants of the new *Petunia* have larger flowers than plants of the male parent selection.

Plants of the new *Petunia* can be compared to plants of *Petunia* X *hybrida* Sanguna® 'Radiant Blue', not patented. In side-by-side comparisons, plants of the new *Petunia* differ primarily from plants of Sanguna® 'Radiant Blue' in the following characteristics:

1. Plants of the new *Petunia* have smaller leaves than plants of Sanguna® 'Radiant Blue'.
2. Leaves of plants of the new *Petunia* are darker green in color than leaves of plants of Sanguna® 'Radiant Blue'.
3. Plants of the new *Petunia* have smaller flowers than plants of Sanguna® 'Radiant Blue'.
4. Flowers of plants of the new *Petunia* have smaller lighter-colored centers than flowers of plants of Sanguna® 'Radiant Blue'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph on the first sheet (FIG. 1) is a side perspective view of a typical flowering plant of 'INPETTIABL' grown in a container.

Figure 2:
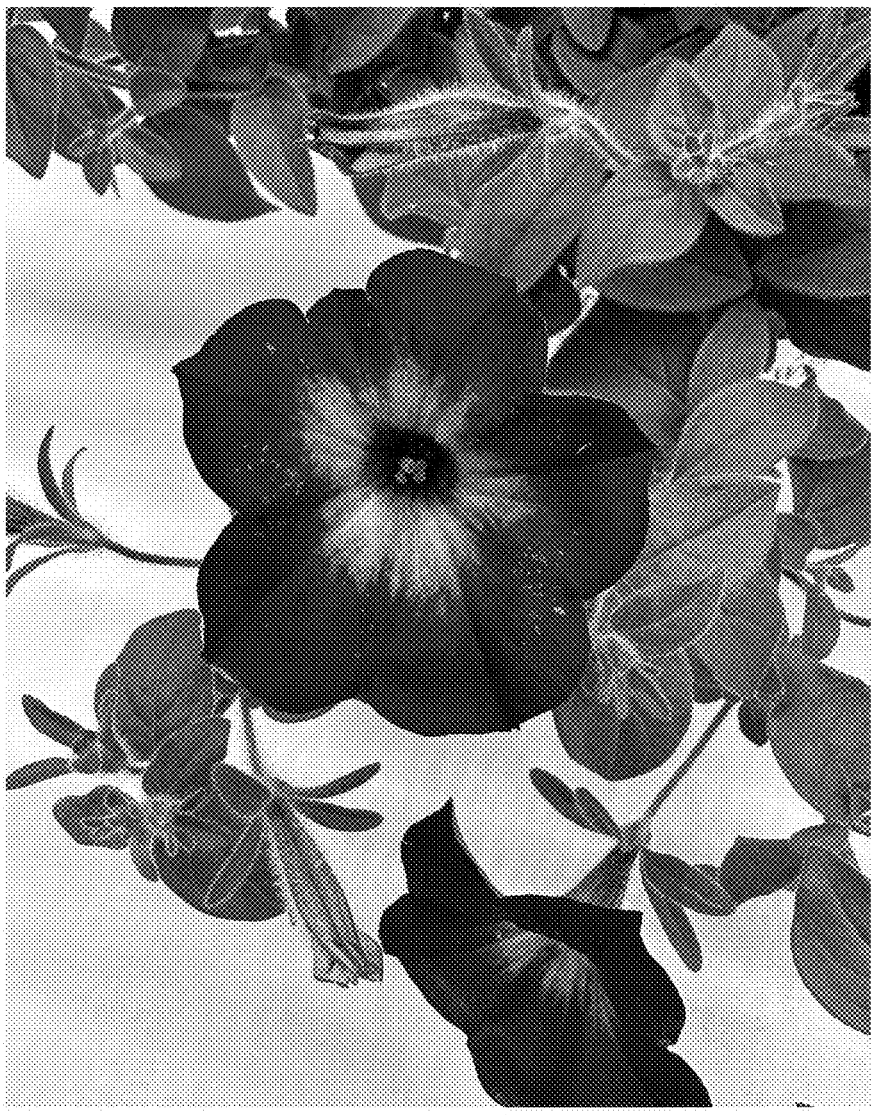

The photograph on the second sheet (FIG. 2) is a close-up view of a typical flowering plant of 'INPETTIABL'.

DETAILED BOTANICAL DESCRIPTION

The aforementioned photographs and following observations and measurements describe plants grown during the late winter and early spring in 10.75-cm containers in a glass-covered greenhouse in Loudon, New Hampshire and under cultural practices typical of commercial *Petunia* production. During the production of the plants, day and night temperatures averaged 20° C. Plants were seven weeks from planting rooted cuttings when the photographs and description were taken. In the following description, color references are made to The Royal Horticultural Society Colour Chart, 2015 Edition, except where general terms of ordinary dictionary significance are used.

Botanical classification: *Petunia* X *hybrida* 'INPETTIABL'.

Parentage:

*Female, or seed, parent*.—Proprietary selection of *Petunia* X *hybrida* identified as code number Pt18-4301-3, not patented.

*Male, or pollen, parent*.—Proprietary selection of *Petunia* X *hybrida* identified as code number Pt18-4313-8, not patented.

Propagation:

*Type*.—Terminal vegetative cuttings.

*Time to initiate roots, summer*.—About two weeks at temperatures about 22° C.

*Time to initiate roots, winter*.—About 18 days at temperatures about ranging from 18° C.

*Time to produce a rooted plant, summer*.—About 20 days at temperatures about 22° C.

*Time to produce a rooted plant, winter*.—About 25 days at temperatures ranging from 18° C.

*Root description*.—Fine, fibrous; typically white in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Upright to outwardly spreading and mounding to eventually trailing and decumbent plant habit; freely branching habit with about nine to ten primary lateral branches with secondary laterals developing potentially at every node, dense and bushy plant form; pinching enhances development of lateral branches; vigorous growth habit and rapid growth rate.

*Plant height*.—About 17 cm to 20 cm.

*Plant diameter* (*area of spread*).—About 35 cm to 38 cm.

*Lateral branches*.—Length: About 16 cm to 20 cm. Diameter: About 3 mm to 4 mm. Internode length: About 1.4 cm to 1.7 cm. Strength: Strong; flexible, not brittle. Aspect: Initially upright then outwardly spreading to eventually trailing and decumbent. Texture and luster: Densely pubescent; pubescence, fine; slightly glossy. Color, developing and developed: Close to 144A.

Leaf description:

*Arrangement*.—Alternate before flowering; opposite after flowers develop; leaves simple.

*Length*.—About 3.8 cm to 4.3 cm.

*Width*.—About 2.7 cm to 3 cm.

*Shape*.—Ovate to elliptic.

*Apex*.—Acute.

*Base*.—Obtuse with cuneate tendencies.

*Margin*.—Entire, slightly undulate.

*Texture and luster, upper and lower surfaces*.—Moderately pubescent, pubescence, minute; matte to slightly glossy.

*Venation pattern*.—Pinnate, arcuate.

*Color*.—Developing leaves, upper and lower surfaces: Close to 146A. Fully developed leaves, upper surface: Close to NN137B; venation, close to 144A. Fully developed leaves, lower surface: Close to 146A; venation, close to between 144A and 146A.

*Petioles*.—Length: About 5 mm. Diameter: About 3 mm. Strength: Strong, flexible. Texture and luster, upper and lower surfaces: Densely pubescent; slightly glossy. Color, upper and lower surfaces: Close to 144A.

Flower description:

*Flower type and flowering habit*.—Single terminal and axillary salverform flowers; flowers face mostly upward to outwardly; freely flowering habit with about 78 developing flowers and open flowers per plant at one time.

*Natural flowering season*.—Long day responsive; long flowering period, plants flower from early spring until frost in the autumn, flowering continuous during this period; early flowering habit, depending on temperature, plants begin flowering about four to six weeks after planting rooted young plants.

*Flower longevity on the plant*.—Depending on temperature, about one to two weeks; petals not persistent, and sepals, persistent.

*Fragrance*.—None detected.

*Flower buds, before showing petal color*.—Length: About 2.2 cm. Diameter: About 4 mm. Shape: Oblong, elongate. Texture and luster: Pubescent; slightly glossy. Color, developing sepals: Close to 144A. Color, developing petals: Close to 83A to 83B.

*Flower diameter*.—Medium-sized, about 4.5 cm to 4.75 cm.

*Flower depth* (*height*).—About 3.5 cm to 3.8 cm.

*Throat diameter*.—About 7 mm to 9 mm.

*Tube length*.—About 2.5 cm to 2.75 cm.

*Tube diameter, distally*.—About 8 mm to 9 mm.

*Tube diameter, proximally*.—About 1.5 mm to 2 mm.

*Petals*.—Quantity and arrangement: Five petals fused in a single salverform whorl. Petal lobe length (from throat): About 1.75 cm to 2.25 cm. Petal lobe width: About 2 cm to 2.25 cm. Petal lobe shape: Roughly spatulate. Petal lobe apex: Broadly obtuse and cuspidate. Petal lobe margin: Entire; moderately undulate. Petal lobe texture and luster, upper surface: Smooth, glabrous; velvety; slightly glossy and iridescent. Petal lobe texture and luster, lower surface: Smooth, glabrous; slightly glossy. Throat texture and luster: Smooth, glabrous; matte. Tube texture and luster: Densely pubescent; matte. Color: When opening and fully opened, upper surface: Close to 86A; towards the throat, a relatively small area, close to 85A variably tinged with close to 86A; venation, similar to lamina colors; colors do not change with subsequent development; under high light conditions, lighter-colored centers may become larger. When opening and fully opened, lower surface: Close to N82A to N82B; venation, close to 144A; color does not change with subsequent development. Flower throat (inside): Distally, close to 86A and proximally, close to N92A; venation, close to N92A. Flower tube (outside): Close to 83A to 83B; venation, close to 144A.

*Sepals*.—Quantity and arrangement: Five, or occasionally six, sepals fused in a single star-shaped whorl; sepals flaring outwardly. Length: About 1.1 cm to 1.4 cm. Width: About 3 mm. Shape: Linear. Apex: Acute. Margin: Entire. Texture and luster, upper surface: Sparsely to moderately pubescent; pubescence, fine; matte to slightly glossy. Texture and luster, lower surface: Moderately pubescent; pubescence, fine; matte to slightly glossy. Color, upper and lower surfaces: Close to between 144A and 146A.

*Peduncles, terminal flowers*.—Length: About 2.4 cm to 2.8 cm. Width: About 1 mm to 1.5 mm. Strength: Moderately strong; wiry and flexible, not brittle. Angle: About 30° to 45° from the stem axis. Texture and luster: Densely pubescent; slightly glossy. Color: Close to 144A.

*Reproductive organs*.—Stamens: Quantity per flower: About five. Filament length: About 1.9 cm to 2.1 cm. Filament color: Close to 157A to 157B. Anther length: About 1 mm. Anther shape: Bi-lobed. Anther color: Close to N82A. Pollen amount: Moderate. Pollen color: Close to 94A to 94B. Pistils: Quantity per flower: One. Pistil length: About 2.5 cm. Style length: About 2.3 cm. Style color: Close to N79A. Stigma diameter: About 1 mm. Stigma shape: Rounded. Stigma color: Close to 79A. Ovary color: Close to 144A.

*Seeds and fruits*.—To date, seed and fruit development has not been observed on plants of the new *Petunia*.

Pathogen & pest resistance: To date, plants of the new *Petunia* have not been noted to be resistant to pathogens or pests common to *Petunia* plants.

Garden performance: Plants of the new *Petunia* have been observed to have excellent garden performance and have been observed to tolerate rain, wind and temperatures ranging from about 4° C. to about 40° C.

It is claimed:

1. A new and distinct *Petunia* plant named 'INPETTIABL' as herein illustrated and described.

* * * * *